United States Patent [19]

Ducommun

[11] 4,198,542
[45] Apr. 15, 1980

[54] DEVICE FOR AIDING PERSONS HAVING A SPEECH HANDICAP

[76] Inventor: Georges Ducommun, St. Niklaus 91, 4532 Feldbrunnen, Switzerland

[21] Appl. No.: 903,549

[22] Filed: May 8, 1978

[30] Foreign Application Priority Data

May 13, 1977 [CH] Switzerland .................. 5987/77

[51] Int. Cl.² .............................................. A61N 1/36
[52] U.S. Cl. ................................. 179/1 AL; 128/774; 128/905
[58] Field of Search ............. 179/1 AL; 128/DIG. 7, 128/2 S, 24.2, 44, 2.05 S, 774, 905

[56] References Cited

U.S. PATENT DOCUMENTS

| | | | |
|---|---|---|---|
| 2,374,090 | 4/1945 | French | 179/1 AL |
| 3,628,538 | 12/1971 | Vincent et al. | 128/2.1 M |

Primary Examiner—Malcolm A. Morrison
Assistant Examiner—E. S. Kemeny
Attorney, Agent, or Firm—Wender, Murase & White

[57] ABSTRACT

A device for aiding persons having a speech handicap, comprising a first transducer capable of picking up and transforming into an electrical signal the vibrations emitted by an element such as one of the vocal chords of the phonation mechanism of the person. In a first embodiment of the invention, the signal is treated by an electronic circuit comprising an amplifier which feeds a second transducer acting on another element such as the other vocal chord of the phonation mechanism so as to facilitate or reinforce the formation of sounds produced by said mechanism; in a second embodiment of the invention, the amplifier is followed by a rectifier feeding the second transducer which produces a mechanical action, like tension, in another element such as a muscle of the phonation mechanism in order to help close the glottis of the handicapped person.

9 Claims, 5 Drawing Figures

DEVICE FOR AIDING PERSONS HAVING A SPEECH HANDICAP

BACKGROUND OF THE INVENTION

The present invention relates to a device for aiding persons having a speech handicap.

It is known that speech depends on at least two independent parameters. One of them determines the level of the sounds emitted and the other the phonetic content of these sounds. The mechanism which monitors the level or frequency of the sounds is called phonation, whilst the mechanism which determines the phonetic content of these sounds is called articulation. In the present specification, only the phonation mechanism will be considered.

The level of the human voice is determined by the larynx in the following manner. An expiration is first necessary to produce a sound. In opposition to the conditions of normal respiration, the glottis, that is to say, the space between the vocal cords, is closed or very greatly restricted. In this manner a higher pressure is produced in the thorax than during normal expiration. This pressure which is exerted on the vocal cords, has the effect of separating the cords from each other so that a flow of air is produced which, passing through the glottis, terminates in the space formed by the throat and mouth. However, the glottis narrows the path for the expired air so that, in this position, the speed of the air is appreciably higher than in the trachea. It follows that the air pressure is very low at the level of the glottis thus permitting the glottis to close again and the phenomena begins all over again.

In other words, the vocal cords vibrate sufficiently to allow the passage between them of puffs of air, the number per second of which represents the level or frequency of the sound emitted. This frequency depends mainly on the tension of the vocal cords and only then on the pressure of air under the glottis. It is clear that these two parameters can be modified by the muscles of the larynx and those of the thorax.

Some diseases of the larynx have an effect on the power of emitting sounds or speech. These are in particular those which concern the vocal cords such as paralysis thereof, the weakness of the muscles determining their tension, and cancer of the larynx which in the first place attacks the vocal cords.

SUMMARY OF THE INVENTION

The object of the present invention is to provide a device for incorporation into the larynx to overcome, at least partially, the harmful effects produced by ailments of the vocal cords thereby improving the production of sounds and making possible almost normal use of speech by a patient afflicted with these ailments.

According to the present invention there is provided a device for aiding persons having a speech handicap, comprising a first transducer capable of picking-up and transforming into an electrical signal the vibrations emitted by the phonation mechanism of the said person, said signal being treated by an electronic circuit which feeds a second transducer capable of acting on one of the members of the said phonation mechanism so as to facilitate or reinforce the formation of sounds produced by the said mechanism; said device being fed by a battery.

The present invention will be described hereinafter, by way of example, with reference to the accompanying drawing.

DESCRIPTION OF THE PREFERRED EMBODIMENTS

Figure 1:
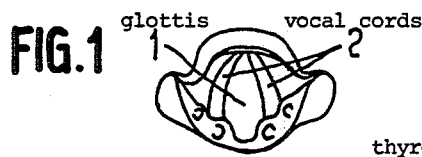
FIG. 1 is a plan view of a larnyx during inspiration with the vocal cords apart.
Figure 2:
FIG. 2 is a plan view of the larynx of FIG. 1 in the position of phonation with the vocal cords closed.
Figure 3:
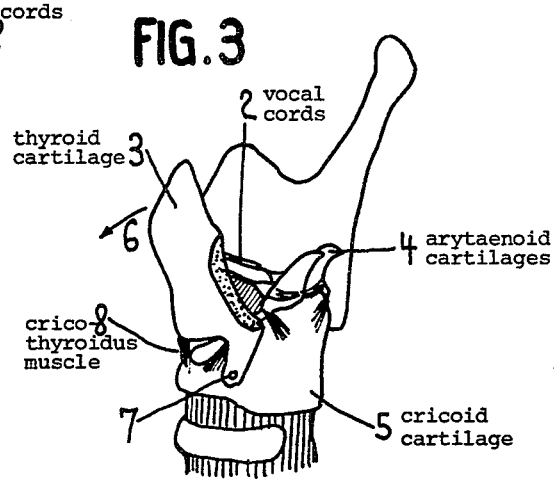
FIG. 3 is a partial perspective view, with parts broken away, of the larynx of FIG. 1 together with its associated muscles.

FIGS. 1 and 2 illustrate a larynx with glottis 1 and the vocal cords 2. In FIG. 1 the vocal cords are shown in the position during inspiration and are separated from each other and the glottis is open. FIG. 2 shows the position of the vocal cords during phonation wherein the vocal cords 2 touch each other and the glottis 1 is closed. FIG. 3 shows a median section of the upper part of the larynx illustrating the vocal cords 2 which are stretched between the thyroid cartilage 3 and the two arytaenoid cartilages 4.

The thyroid cartilage 3 can effect the following movements relative to the cricoid cartilage 5:
(a) forward sliding; and
(b) a downward swing 6 about the axis 7.

Both the arytaenoid cartilages rest on the strip of cricoid cartilage and they can effect the following movements:
(a) turning around their longitudinal axis;
(b) sliding on the strip of cricoid cartilage so as to separate from each other or to come close together; and
(c) swinging forwardly.

The tension of the vocal cords is regulated, on the one hand, by the crico-thyroidus muscle 8 which swings the thyroid cartilage forwardly, in the direction shown by the arrow 6, thus separating this cartilage from the arytaenoid cartilage, increasing the tension of the vocal cords and, on the other hand, by the vocal muscles which are within the vocal cords and the contraction of which increases the elacticity module and, consequently, the tension of the said vocal cords.

Figure 4:
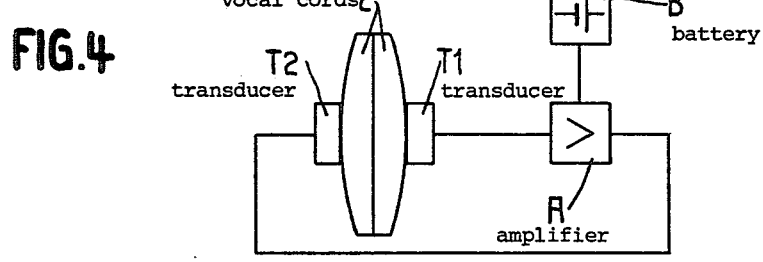
FIG. 4 is a block diagram of one embodiment of a device according to the present invention shown schematically in association with the vocal chords of the larynx of FIGS. 1-3.

FIG. 4 is a block diagram of an embodiment of the device forming the subject of the invention. The vocal cords 2 are shown and a first transducer T1 is located on the right vocal cord. In this embodiment it is assumed that, as a result of one of the diseases mentioned above, the tension on the left vocal cord is insufficient to produce a normal sound. The patient can no longer speak normally, the intensity of his voice being too weak. The transducer T1, which is of the inertia type, for example having a vibrating blade, picks up the weak vibration of the vocal cord to which it is secured and delivers an electrical signal of the same frequency as said cord. This signal is amplified by an amplifier A, incorporated in the larynx or in the proximity thereof, and transmits it to a transducer T2, of electro-mechanical type, for example with a moving coil, located on the left vocal cord. The vibration of T2 is then transmitted to the said vocal cord, compelling it to vibrate at the same frequency and with an amplitude sufficient to re-establish almost normal conditions of phonation. The device is fed by a battery B.

Figure 5:
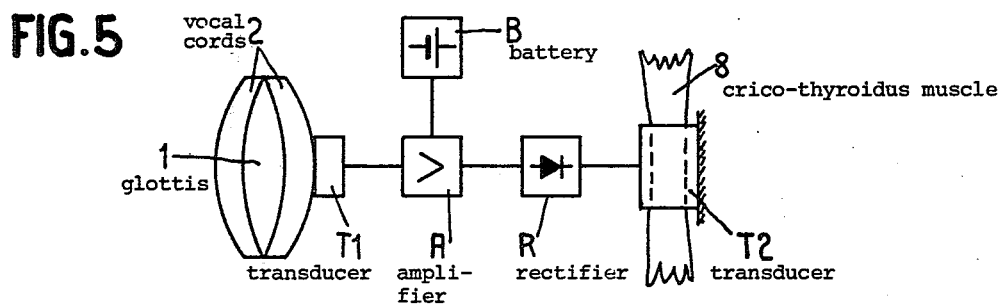
FIG. 5 is a block diagram of another embodiment of the device according to the present invention.

It is obvious that other possibilities of using the device may be proposed, as for example in the embodiment of FIG. 5. In this example, the glottis 1 is not completely closed, the vocal cords 2 not being sufficiently stretched due to the fact that the crico-thyroidus muscle 8, controlling the swinging of the thyroid cartilage is atrophied or partially paralysed. As in the preceding case, the patient can no longer speak normally, his voice being too weak. The transducer T1, of the inertia type, picks up the weak vibration of the right vocal cord to which it is secured and transmits an electrical signal of the same frequency. This signal is amplified by the amplifier A and rectified by the rectifier R which transmits a continuous output signal, the value of which being proportional to the amplitude of the vibration of the right vocal cord. This continuous signal feeds the electro-mechanical transducer T2 which is secured between the crico-thyroid muscle 8 and a fixed part of the larynx. The transducer T2 increases the tension of the muscle 8, so that the thyroid cartilage swings normally, the result of which is to stretch the vocal cords and close the glottis 1. In this manner, the strength of the patient's voice becomes almost normal again. The device is fed by the battery B.

Other embodiments of the device may be proposed without departing from the scope of the invention. Thus, for example, it is also possible to provide the second transducer T2 in the form of a probe implanted in a suitable manner in one of the vocal cords or in one of the other muscles of the mechanism of phonation, for the purpose of exerting an action tending to stretch this muscle. The probe may be fed, as desired, by an alternating signal at the frequency of the vibration of the vocal cords or by a continuous voltage or be pulsed. It is also possible to envisage the said probe being implanted in the same vocal cord as that to which the transducer T1 is secured. In this case, by creating positive reaction, the vibration of the said vocal cord can be appreciably reinforced.

I claim:

1. A device for aiding persons having a speech handicap due to a dysfunctional phonation muscle, comprising:
   first transducer means for picking up and transforming vibrations emitted by a functional phonation muscle of said person into an electrical signal;
   circuit means coupled to said transducer means for producing an electrical correction signal representative of said electrical signal; and
   second transducer means coupled to said circuit means for stimulating said dysfunctional phonation muscle thereby to correct the speech handicap.

2. A device according to claim 1, wherein said first transducer means is of the inertia type.

3. A device according to claim 1, wherein said second transducer means is of the electromechanical type.

4. A device according to claim 1, wherein said second transducer means is responsive to said electrical correction signal for transmitting vibrations of acoustic frequency to said dysfunctional phonation muscle.

5. A device according to claim 1, wherein said second transducer means is responsive to said electrical correction signal for transmitting to said dysfunctional phonation muscle a continuous signal of a value proportional to the amplitude of said vibrations of said functional phonation muscle.

6. A device according to claim 1, wherein said second transducer means comprises a probe for implantation into said dysfunctional phonation muscle to increase the tension thereof in response to said electrical correction signal.

7. A device according to claim 1, wherein said circuit means comprises an amplifier for the signals of said first transducer means.

8. A device according to claim 1, wherein said circuit means comprises an amplifier and a rectifier for the signals of said first transducer means.

9. A device according to any one of claims 1 to 8, wherein said first and second transducer means comprise implantation transducers for direct connection to said functional and dysfunctional phonation muscles, respectively, and wherein said circuit means includes a battery for supplying operating potential to the device, said circuit means and said battery being implantable in the larynx of said person.

* * * * *